March 15, 1966 L. B. ELLIS Plant Pat. 2,608
APPLE TREE
Filed Dec. 22, 1964
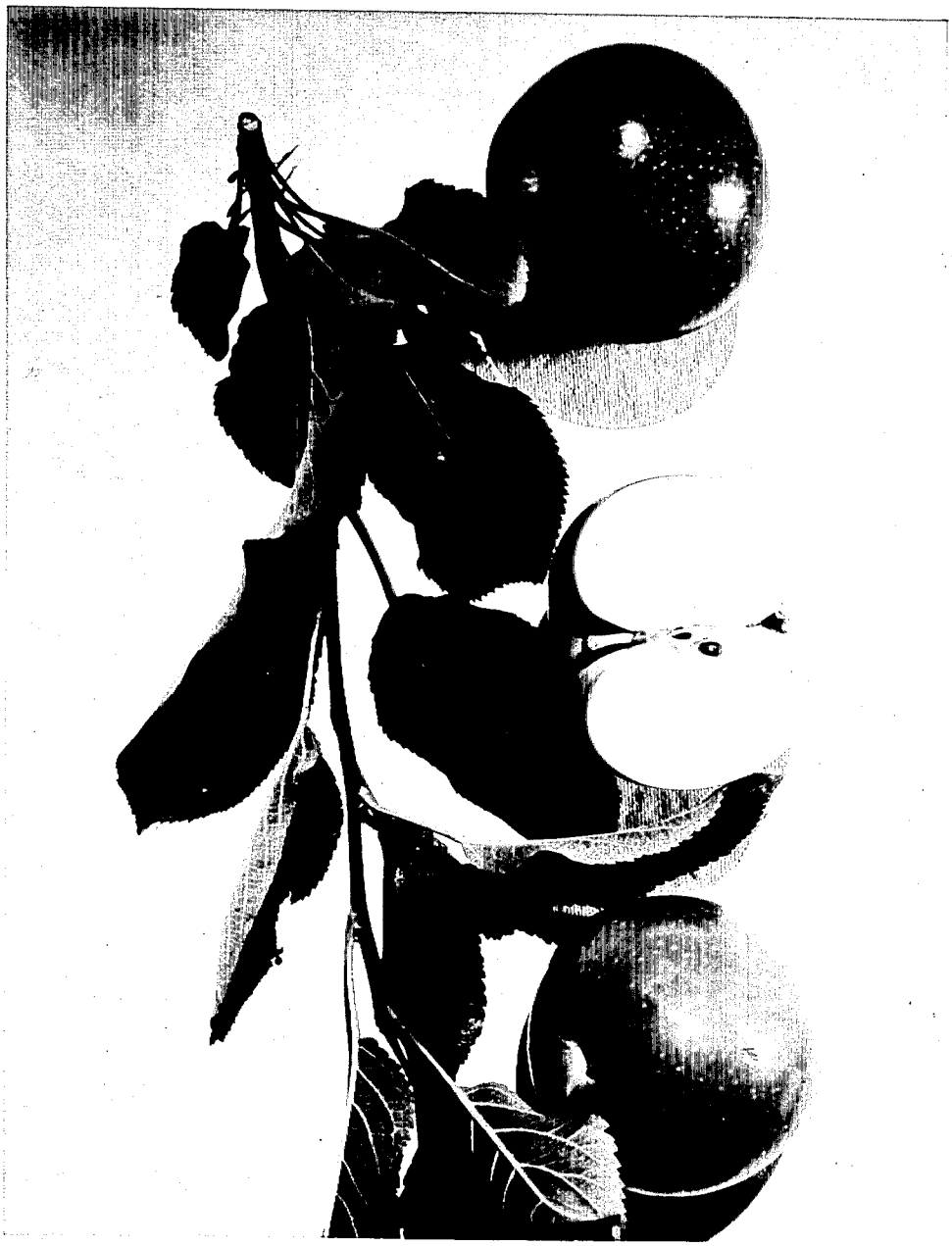
Inventor
Lura B. Ellis
By: Robb & Robb
Attorneys.

United States Patent Office

Plant Pat. 2,608
Patented Mar. 15, 1966

2,608
APPLE TREE

Lura B. Ellis, Bone Gap, Ill., assignor to Stark Bro's Nurseries & Orchards Company, Louisiana, Mo., a corporation of Missouri Filed Dec. 22, 1964, Ser. No. 420,468
1 Claim. (Cl. Plt.—34)

The present invention relates to a new and distinct variety of apple tree which was discovered by me as a newly found seedling of unknown parentage in my cultivated garden on my property at Bone Gap, Illinois.

At the time of my discovery aforesaid, my attention was attracted to the new seedling by reason of the fact that it bore fruit which was generally similar to that of the variety known as "Jonalicious" (Plant Patent No. 1,777), but which ripened approximately two weeks earlier than the fruit of that variety. Further study and tests of the new seedling revealed that in addition to the earlier ripening habit just referred to, the fruit of the new variety was of high quality, had a deep, acute basin and a smoother finish than the fruit of "Jonalicious," and further the flavor of the fruit was more acid and the fruit had a more attractive bright red color. The new variety was also found to be very productive and consequently suitable for the production of commercial apple crops.

Asexual reproduction of my new variety, as performed on my behalf by budding in Pike County, Missouri, confirmed that the foregoing characteristics come true and are established and transmitted through succeeding propagations. Despite the uncertainty of the parentage of my new seedling, I am convinced that it represents a new and distinct variety and is differentiated from all other varieties by the unique combination of characteristics referred to in the foregoing.

The accompanying drawing shows typical specimens of the fruit and foliage of the new variety as depicted in color as nearly true as it is reasonably possible to make the same in a color illustration of this character, with certain of the fruit specimens being shown in top and bottom perspective, and one of the fruit specimens being shown in longitudinal cross-section.

The following is a detailed description of my new variety, with color terminology in accordance with Ridgway's Color Standards and Nomenclature, except where general color terms of ordinary dictionary significance are obvious:

Locality where grown and observed: Louisana, Pike County, Missouri.

Date of first and last pickings: About August 27 and about September 5, respectively.

Tree: Medium-large size; vigorous; spreading; medium-tall; open; rapid growing; hardy; productive; regular bearer.

*Trunk.*—Medium stockiness; smooth.

*Branches.*—Medium thickness; smooth; much-branched. Color—Hessian Brown; Plate XIII, hue 5′, tone M.

*Lenticels.*—Medium number; small.

*Leaves.*—Medium small; medium width; medium length; ovate; abruptly pointed; medium thickness; rugose. Length—about 3 inches. Width—about 1¾ inches. Color—Empire Green, Plate XXXII, hue 33′, tone M. Margin—coarsely serrate. Petiole—medium length (about 1 inch); medium thickness.

Flowers: Medium-late, as compared with other varieties; medium large.

*Dates of first and full bloom.*—About April 18 and about April 20, respectively.

*Color.*—White.

Fruit:

*Maturity when described.*—Hard ripe (August 29).

*Size.*—Uniform. Axial diameter—from about 2½ inches to about 2¾ inches. Transverse diameter—from about 3 inches to about 3⅜ inches.

*Form.*—Globose at both base and apex.

*Cavity.*—Symmetrical at base; rounded; even toward apex, with apex acute. Depth—about ¾ inch. Breadth—about 1¼ inches. Markings—color—Dark Olive Buff, Plate XL, hue 21‴.

*Basin.*—Symmetrical; abrupt at base; even. Depth—about ¼ inch. Breadth—about 1 inch. Markings—none.

*Stem.*—Medium stout; pubescent. Length—about ⅝ inch. Breadth—about 3/16 inch.

*Calyx.*—Closed; segments persistent; narrowly lanceolate; acute; about ¼ inch long; approximate at base; prostrate; reflexed from base, both outer surface and inner surface pubescent.

*Skin.*—Thin; tough; smooth; waxed. Dots—conspicuous; many; small; depressed; circular; color—Cream Color, Plate XVI, hue 19′, tone L; distribution—most numerous toward cavity. Ground color—Primrose Yellow, Plate XXX, hue 23″, tone D. Color markings—bright; self-colored; color—Carmine, Plate I, hue 1, tone *i*. Bloom—scant. General color effect—bright red.

*Flesh.*—Juicy. Color—satiny, with yellowish-white tint. Texture—firm; tender; fine; crisp. Flavor—subacid. Aroma—distinct. Quality—best.

*Core.*—Median. Bundle area—small; oblate; symmetrical at base; acute at base. Halves of core—unequal. Bundles—inconspicuous; in one whorl; color—yellowish tinge. Core lines—clasping; indistinct. Carpellary area—indistinct; small. Calyx tube—pubescent; apex broadly cone-shaped; depth—about ⅜ inch. Styles—present. Stamens—in one distinct whorl; median. Seed cells—axile; partly open. Cell walls—approximate; length—about 9/16 inch; breadth—about 5/16 inch. Longitudinal section—broadly oval; acute at apex. Surface—fissured. Cross section—narrow.

Seeds:

*Number.*—Usually from 8 to ten, with usually 2 seeds per cell.

*Length.*—About 5/16 inch.

*Breadth.*—About 3/16 inch.

*Form.*—Acute.

*Color.*—Chestnut Brown, Plate XIV, hue 11′. tone M.

Use: Market; dessert; culinary.

Keeping quality: Good; fruit keeps about 120 days in ordinary storage.

Disease resistance: Good resistance to infection attributed to bacterial fire blight.

I claim:

A new and distinct variety of apple tree, substantially as herein shown and described, characterized particularly as to novelty by its general resemblance to the variety "Jonalicious" (Plant Patent No. 1,777), but having very productive habit and bearing fruit of high quality, said fruit having a deep, acute basing and a smooth finish than the fruit of "Jonalicious," said fruit ripening approximately two weeks earlier than "Jonalicious," being larger in size, somewhat more acid and having a more attractive bright red color.

No references cited.

ABRAHAM G. STONE, *Primary Examiner.*